(12) United States Patent
Lalicki et al.

(10) Patent No.: US 9,439,989 B2
(45) Date of Patent: Sep. 13, 2016

(54) DISINFECTING LIGHT FIXTURE

(71) Applicant: Vital Vio, Inc., Troy, NY (US)

(72) Inventors: Jorel Lalicki, Tivoli, NY (US); James W. Peterson, Falls Church, VA (US)

(73) Assignee: Vital Vio, Inc., Troy, NY (US)

( * ) Notice: Subject to any disclaimer, the term of this patent is extended or adjusted under 35 U.S.C. 154(b) by 0 days.

(21) Appl. No.: 14/812,152

(22) Filed: Jul. 29, 2015

(65) Prior Publication Data

US 2016/0030609 A1 Feb. 4, 2016

Related U.S. Application Data

(63) Continuation-in-part of application No. 14/501,931, filed on Sep. 30, 2014.

(60) Provisional application No. 62/031,434, filed on Jul. 31, 2014.

(51) Int. Cl.
*A61L 2/08* (2006.01)
*F21V 23/00* (2015.01)
(Continued)

(52) U.S. Cl.
CPC . *A61L 2/08* (2013.01); *A01G 9/26* (2013.01); *A01K 1/0047* (2013.01); *A01K 29/00* (2013.01);
(Continued)

(58) Field of Classification Search
CPC ........... A61L 2/08; A61L 9/18; A61L 2/084; A61L 2202/24; A01G 9/26; A01K 29/00; A01K 1/0047; A01M 21/046; A01M 19/00; A01M 63/06; F21V 23/003; F21K 9/56; F21W 2131/405; F21W 2131/208; F21Y 2113/005; F21Y 2113/02; F21Y 2101/02; H01L 25/0753; H01L 27/153; H01L 27/156; H01L 33/08; A61N 2005/0662; A61N 5/0624; A61N 2005/0642; A61N 2005/0651; A61N 5/0613

USPC ....... 362/84, 231, 293, 362; 257/89; 422/24, 422/186.3; 250/492.1
See application file for complete search history.

(56) References Cited

U.S. PATENT DOCUMENTS

| 3,670,193 A | 6/1972 | Thorington et al. |
| 3,992,646 A | 11/1976 | Corth |

(Continued)

FOREIGN PATENT DOCUMENTS

| EP | 1693016 A1 | 8/2006 |
| EP | 1887298 A1 | 2/2008 |

(Continued)

OTHER PUBLICATIONS

Color Phenomena, "CIE-1931 Chromaticity Diagram," last updated Aug. 22, 2013, retrieved from www.color-theory-henomena.nl/10.02.htm on Jan. 20, 2016, 3 pages.

(Continued)

*Primary Examiner* — Evan Pert
*Assistant Examiner* — Changhyun Yi
(74) *Attorney, Agent, or Firm* — Hoffman Warnick LLC (57) ABSTRACT

Disclosed herein is a light fixture. The light fixture includes at least one first light source that emits at a peak wavelength in a range of approximately 380 nm to approximately 420 nm and at least one second light source that emits at a different peak wavelength, wherein a combined light output of the at least one first light source and the at least one second light source emits a colored light that is perceived as white light. The white light is defined by having a color rendering index (CRI) value of more than approximately 50. The at least one second light source that emits at a different peak wavelength consists of an xy coordinate on a International Commission on Illumination (CIE) 1931 xy color space diagram above a black body curve within a bounded area defined by a first line of approximately $y=2.23989x-0.382773$ and a second line of approximately $y=1.1551x-0.195082$. The combined light output has a proportion of spectral energy measured in the approximately 380 nm to approximately 420 nm range of greater than approximately 20%.

24 Claims, 4 Drawing Sheets
(2 of 4 Drawing Sheet(s) Filed in Color)

(51) Int. Cl.
*F21K 99/00* (2016.01)
*A01M 19/00* (2006.01)
*A01M 21/04* (2006.01)
*A01G 9/26* (2006.01)
*A01K 1/00* (2006.01)
*A01K 29/00* (2006.01)
*A01K 63/06* (2006.01)
*F21Y 101/02* (2006.01)
*F21Y 113/02* (2006.01)
*F21W 131/208* (2006.01)
*F21W 131/405* (2006.01)
*F21Y 113/00* (2016.01)

(52) U.S. Cl.
CPC .............. *A01K 63/06* (2013.01); *A01M 19/00* (2013.01); *A01M 21/046* (2013.01); *F21K 9/56* (2013.01); *F21V 23/003* (2013.01); *F21W 2131/208* (2013.01); *F21W 2131/405* (2013.01); *F21Y 2101/02* (2013.01); *F21Y 2113/005* (2013.01); *F21Y 2113/02* (2013.01)

(56) References Cited

U.S. PATENT DOCUMENTS

| | | |
|---|---|---|
| 6,791,259 B1 | 9/2004 | Stokes et al. |
| 8,398,264 B2 | 3/2013 | Anderson et al. |
| 8,476,844 B2 | 7/2013 | Hancock et al. |
| 8,508,204 B2 | 8/2013 | Deurenberg et al. |
| 2003/0124023 A1 | 7/2003 | Burgess et al. |
| 2004/0008523 A1 | 1/2004 | Butler |
| 2005/0055070 A1 | 3/2005 | Jones et al. |
| 2005/0207159 A1 | 9/2005 | Maxik |
| 2006/0262545 A1 | 11/2006 | Piepgras et al. |
| 2008/0008620 A1 | 1/2008 | Alexiadis |
| 2008/0278927 A1 | 11/2008 | Li et al. |
| 2009/0034236 A1 | 2/2009 | Reuben |
| 2010/0090935 A1* | 4/2010 | Tseng .................. C09K 11/7721 345/83 |
| 2012/0320607 A1 | 12/2012 | Kinomoto et al. |
| 2013/0077299 A1 | 3/2013 | Hussell et al. |
| 2014/0209944 A1* | 7/2014 | Kim ...................... H01L 33/28 257/89 |
| 2014/0254131 A1 | 9/2014 | Osinski et al. |
| 2014/0328046 A1* | 11/2014 | Aanegola .................. F21K 9/00 362/84 |
| 2016/0091172 A1* | 3/2016 | Wu ........................... F21V 9/16 362/293 |

FOREIGN PATENT DOCUMENTS

| | | |
|---|---|---|
| EP | 1943880 B1 | 4/2013 |
| JP | 2003339845 A | 12/2003 |
| WO | 0114012 A1 | 3/2001 |
| WO | 03063902 A2 | 8/2003 |
| WO | 2004033028 A2 | 4/2004 |
| WO | 2006100303 A2 | 9/2006 |
| WO | 2006126482 A1 | 11/2006 |
| WO | 2007012875 A1 | 2/2007 |
| WO | 2009056838 A1 | 5/2009 |

OTHER PUBLICATIONS

Patent Cooperation Treaty, Written Opinion of the International Searching Authority and International Search Report for PCT/US2015/042678 date of mailing Nov. 2, 2015, 13 pages.

Yi, Notice of Allowance and Fee(s) Due for U.S. Appl. No. 14/501,931 dated Jan. 20, 2016, 8 pages.

Patent Cooperation Treaty, International Preliminary Report on Patentability for PCT/GB2008/003679 dated May 4, 2010, 9 pages.

Patent Cooperation Treaty, Written Opinion of the International Searching Authority and International Search Report for PCT/GB2008/003679 dated Mar. 3, 2009, 11 pages.

Yi, Office Action Communication for U.S. Appl. No. 14/501,931 dated Jul. 21, 2015, 19 pages.

* cited by examiner

DISINFECTING LIGHT FIXTURE

CROSS-REFERENCE TO RELATED APPLICATIONS

This application is a Continuation-In-Part of U.S. application Ser. No. 14/501,931 filed 30 Sep. 2014, which claims the benefit of U.S. Provisional Application Ser. No. 62/031,434, filed 31 Jul. 2014, which is hereby incorporated by reference herein.

TECHNICAL FIELD DISCLOSURE

The present disclosure concerns solid-state lighting devices that provide high-quality lighting along with environmental decontamination with white light, based on visible light disinfection technology. Generally, the disclosure relates to the use of visible light, in the wavelength ($\lambda$) range of approximately 380 to approximately 420 nanometers (nm), in combination with at least one secondary wavelength to create white light, that can reduce or eliminate bacterial, fungal, and/or viral contamination on environmental surfaces.

BACKGROUND OF THE DISCLOSURE

Generally, different forms of light can be used in many different applications. Through the delivery of specific wavelengths of light, effects such as the inactivation of bacteria, fungi, or viruses can be accomplished, chemical reactions, such as the curing of plastics or other materials can be caused, heat can be generated, and the wavelength of the light can be converted to an alternative wavelength.

White light is generally composed of multiple wavelengths of light from across the visible spectrum. White light is generated though perception of the human eye by the sensitization of the S, M and L cones (short, medium, and long, respectively) which react to wavelengths most commonly described as blue, green, and red, respectively. By having a light source generating wavelengths in each of these cones at proper intensities, white light is perceived by the human eye. To perceive white light, all three cone types must be stimulated.

Typically, a minimum of three colors across the visible spectrum must be used to stimulate the three cone types, as in, for example, of red, green, and blue (RGB) color mixing to produce white light. Additional methods of color mixing, such as blue light pumped phosphors, using two sources of light, one in the blue range, and an additional phosphor that creates light across multiple colors can also accomplish appropriate stimulation of the three cone types, to be perceived as white light. The addition of other wavelengths of light can improve the color rendering index (a rating of quality associated with white light).

Some specific wavelengths of visible light can be used for active reasons beyond general illumination. For example, activation of fluorescent materials can be achieved with approximately 400 to approximately 420 nm range, similar to UVA, or a "black light," curing of plastics can be achieved with approximately 380 to approximately 420 nm light, heat delivery can be achieved with near-infrared approximately 650 to approximately 700 nm light, and inactivation of bacteria can be achieved with near-infrared approximately 650 to approximately 700 nm light. As used herein, unless otherwise specified, approximately can include plus or minus 5 nm.

Regarding inactivation of bacteria, the United States Center for Disease Control (CDC) has reported that every year, 1.7 million hospital patients (about one in every twenty admitted) contract a hospital-acquired infection (HAI) in the United States from bacterial, viral, or fungal microorganisms. These infections result in almost 100,000 deaths, 35-45 billion US$ in excess costs and 25.9 million wasted patient bed days due to the excess costs and time associated with HAIs. Because these infections are deemed "preventable" by the CDC and the US Medicare system, costs associated with such HAIs fall directly on the hospitals. Of hospitals nationwide, 78% have what the CDC considers an infection problem with the rates of infection they see annually. Additionally, in the 16,000 nursing homes in the US, the problem is similar.

In addition to those direct operating costs, current and emerging government regulations (such as the Affordable Care Act) and standards of care are demanding reductions in infections across the nation, yet existing practices and products are still lacking in efficacy. Starting in 2014 the US Affordable Care Act will impose 1-3% reductions in US Medicare reimbursements to hospitals that do not meet appropriate infection standards. Similar regulations may exist in other countries.

Hospital reputation is also becoming increasingly transparent with publicly available data allowing consumers to make decisions about hospitals. Infection rates are publicly available for most hospitals in the US; a hospital with high infection rates may drive away potential "customers." Serious litigation costs in severe cases can also add to the 'price' of infections acquired in a healthcare facility.

Environmental contamination in hospital environments is a key factor in the source of these HAIs, among others. Current methods of attacking environmental contamination range widely, from traditional mopping and surface cleaning to the use of burst ultraviolet (UV) and hydrogen peroxide vapor. Yet, in full force application, infections are still a reality in almost every hospital.

In the cultivation of livestock and agricultural products, contamination from bacteria, fungi, or viruses can cause losses of animal life, plant life, and/or spoilage of rendered products. Common production practices now pack animals and plants densely for efficiency, in terms of space and finances, yet contamination from microorganisms can spread rapidly in such an environment, with infection spreading between plants or animals.

Currently, there is extensive use of pesticides, antibiotics, and chemical cleaners to prevent loss of final product by preventing contamination of animals or agriculture products, yet animal and plant losses, final product losses, and the unknown distribution of contaminated final products is still an issue faced by the industry. Thus, there is a continuing need for better methods to control microorganisms in the cultivation environment and processing facilities to prevent loss of final product.

In the retail sale of food, fresh products are commonly displayed to customers in the shopping environment. In many retail stores, the products are stored on shelves and in cases with viewing windows. Many of these products are considered perishable, with a very short shelf life like meat, produce, or fish. The short shelf life of these items is due to the degradation of the quality of the product over the time displayed. This degradation of the product is caused by a variety of factors: breakdown of cells or molecules due to aging, loss of water or other volatile components into the air, or spoilage based on bacterial, fungal, or viral contamination.

Controlled environments are required for many purposes, such as the preservation of food products, the aging of goods, such as wines, liquors, and tobacco products, or the general prevention of contamination during many industrial processes. Such environments are protected and controlled in many different manners, including in terms of air quality, temperature, humidity, and particle count.

Perishable food is commonly stored in refrigerated enclosures to slow degradation of the food and to slow bacterial growth that can cause food spoilage and food sickness. While refrigeration alone can extend food life and quality, compared with room temperature storage, bacteria and molds can still be common destroyers of food in these environments, in a home refrigerator just as in an industrial meat locker.

Humidors are humidity controlled environments, commonly associated with the storage or aging of cigars and tobacco products, that maintain moisture content at a set level for the items stored in the enclosure. However, bacterial and mold spoilage of these goods can occur in the event of contamination, resulting in the loss of what is typically a high value product.

In clean rooms, efforts are made to control the amount of particles in the air in a given enclosure. Most function by continuously pumping in filtered air and forcing the exodus of airborne particles. Bacterial growth and the generation of bacteria or mold spores from contaminated sites can continuously generate particles in the environment that can be difficult to prevent and cause costly contamination issues in high-value products undergoing processing or storage in the environment.

In a food preparation environment (e.g., restaurants, industrial kitchens, fast food, prepared goods store, for direct sale or delivery to the consumer/customer) bacteria, fungi, and/or viruses pose issues of spoilage, pathogenic contamination, and infection, and can be a serious issue for the establishment. These contamination issues can come from a large variety of sources in such an open environment: e.g., personnel, customers, raw materials, air systems, and water. While many cleaning practices have typically been implemented at these sites, contamination and infection outbreaks are still seen. Typically, these contamination issues are only noticed after the damage is done, when inventory is spoiled or customers are sick.

UV light can be used for disinfection in an industrial environment, but not in environments where personnel would also be exposed to the light, for safety reasons. This greatly limits the ability to create a consistently protected environment against bacteria. UV light also has known detrimental effects on plastics, proteins, and DNA, potentially degrading goods, raw materials, packaging, and equipment in the industrial environment.

Loss of goods and raw materials occurs in many industrial processes because of bacterial, viral, or fungal infections or contamination, including, but not limited to, pharmaceuticals, brewing/distillation, food production, food packaging, chemical processing, and semiconductor processing steps requiring a clean room environment.

BRIEF DESCRIPTION OF THE DISCLOSURE

Embodiments of the disclosure may include a light fixture comprising: at least one first light source that emits at a peak wavelength in a range of approximately 380 nanometers (nm) to approximately 420 nm; at least one second light source that emits at a different peak wavelength, wherein a combined light output of the at least one first light source and the at least one second light source emits a colored light that is perceived as white light; wherein the white light comprises a color rendering index (CRI) value of more than approximately 50; wherein the at least one second light source that emits at a different peak wavelength consists of: an xy coordinate on a International Commission on Illumination (CIE) 1931 xy color space diagram above a black body curve within a bounded area defined by a first line of approximately y=2.23989x−0.382773 and a second line of approximately y=1.1551x−0.195082; and wherein the combined light output has a proportion of spectral energy measured in the approximately 380 nm to approximately 420 nm range of greater than approximately 20%.

BRIEF DESCRIPTION OF THE DRAWINGS

These and other features of the disclosure will be more readily understood from the following detailed description of the various aspects of the disclosure taken in conjunction with the accompanying drawings that depict various aspects of the disclosure.

The patent or application file contains at least one drawing executed in color. Copies of this patent or patent application publication with color drawing(s) will be provided by the Office upon request and payment of the necessary fee.

It is noted that the drawings may not be to scale. The drawings are intended to depict only typical aspects of the disclosure, and therefore should not be considered as limiting the scope of the disclosure. In the drawings, like numbering represents like elements between the drawings. The detailed description explains embodiments of the disclosure, together with advantages and features, by way of example with reference to the drawings.

DETAILED DESCRIPTION OF THE DISCLOSURE

In addition to the above disclosed uses of light in the disclosed wavelengths, the light, in embodiments of the disclosure, can be utilized for the inactivation of bacterial pathogens with a peak wavelength of light, or in some embodiments, multiple peak wavelengths, in a range of approximately 380 nm to approximately 420 nm, for example, approximately 405 nm light may be used as the peak wavelength. It should be understood that any wavelength within 380 nm to 420 nm may be utilized, and that the peak wavelength may include a specific wavelength plus or minus approximately 5 nm.

Because these wavelengths are in the visible spectrum, they can be paired with additional colors in the visible spectrum to stimulate the three tristimulus receptors of the human eye to form what is perceived as white light in a method similar to RGB color mixing, or the mixing of red, green, and blue light. White light can have a number of definitions, but as used within this disclosure, white light is generally defined as light with a color rendering index (CRI) value of at least 50. In some embodiments, the CRI value may include at least 55, 60, 65, 70, 75, 80, 85, 90, or at least 95, and up to approximately 100. The CRI value may include a variance of plus or minus approximately 5. Further, white light can be defined as light with a correlated color temperature (CCT) value of approximately 1000 kelvin (K) to approximately 8000K, or in some embodiments approximately 2000K to approximately 6000K, wherein approximately can include plus or minus about 200K, or plus or minus about 500K.

Figure 1:
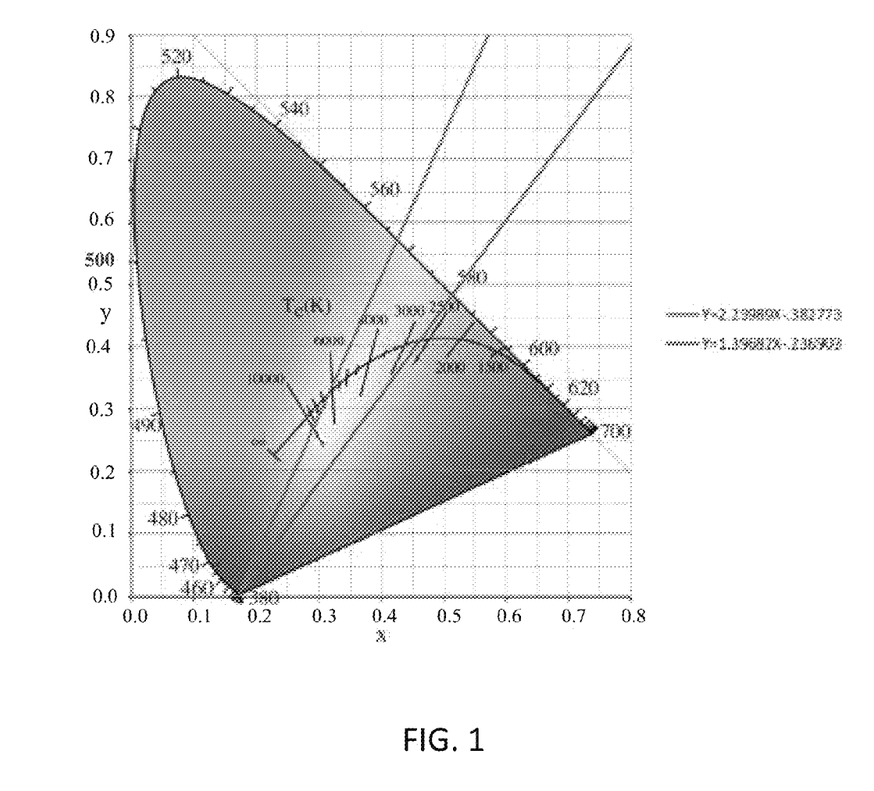
FIG. 1 illustrates a color spectrum according to some embodiments of the disclosure.
Figure 4:
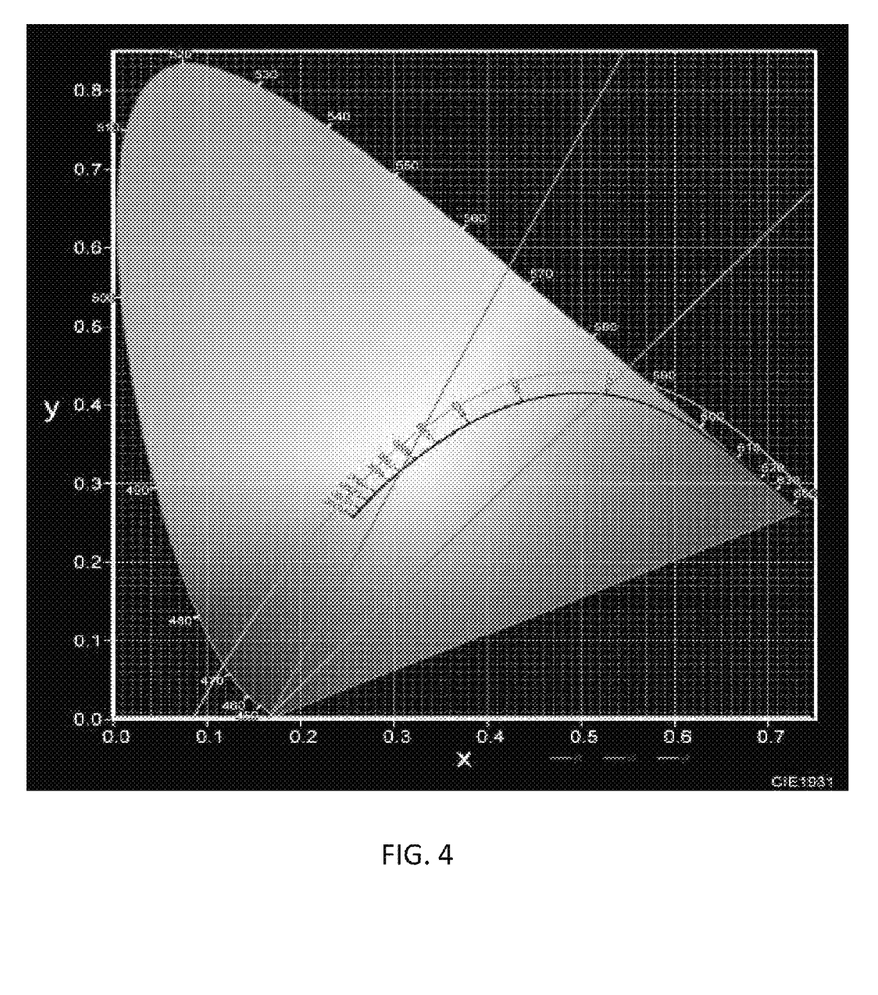
FIG. 4 illustrates a color spectrum according to further embodiments of the disclosure.

Additionally, white light according to some embodiments of the disclosure may be defined using the International Commission on Illumination (CIE) 1931 xy color space, which is a mathematically defined color space for which an equation defines the intended colors on a chromaticity diagram as illustrated in FIG. 1. Turning to FIG. 1, in these embodiments, white light may be defined as a combination of at least one first light source with a peak wavelength within a range of 380-420 nm, as described above, combined with at least one second light source, which is further described below, in order to produce a combined light output that is perceived as a white light. The second light source(s) may comprise a color point, or an xy coordinate, on the CIE 1931 xy color space with a color point within the bounded area of the two lines shown, $y=2.23989x-0.382773$ and $y=1.1551x-0.195082$, and above the black body curve of the diagram. In some embodiments, the at least one second light source may comprise an xy coordinate on the International Commission on Illumination (CIE) 1931 xy color space diagram within a bounded area defined by a first line of approximately $y=2.23989x-0.382773$, a second line of approximately $y=1.1551x-0.195082$, and above a third line of approximately $y=-2.57862x^2+2.58744x-0.209201$ (grey line in FIG. 4), which is within the above defined bounded area as seen in FIG. 4. It should be understood that any one of the CRI value, CCT value, and CIE xy coordinate may be used alone or together in order to define white light according to embodiments of the disclosure.

Additionally, many of these active wavelengths, such as those from a first light source with a peak wavelength of approximately 380-420 nm, are at or near the far ends of the visible spectrum. As such, they have relatively low luminous efficiency in the human eye, and are thus not viewed by humans as being as intense as other light within the visible spectrum.

In pairing with additional colors in the spectrum to generate what is perceived as white light, these wavelengths must be at much higher radiant intensities to match the illuminance of the other colors of higher luminous efficiency wavelengths. This allows for an overall white light to be perceived that also delivers a high radiometric output of these active wavelengths, compared with other additional colors, while not affecting the luminous output of the combined spectra.

Using visible wavelengths of light, these actions can be accomplished safely around humans and animals, and with the addition of complementary wavelengths of light to complete the tristimulus of the human eye, the overall output from a device emitting high energy density white light, can be perceived by the human eye as white, and can be used for general or task illumination.

Embodiments of the present disclosure include solid-state lighting (SSL) products that offer the benefits of high-quality (e.g., high CRI) light output while also reducing environmental bacteria markedly over a period of time.

Embodiments of the present disclosure can include visible light disinfection fixtures and methods which can fulfill the need for continuous decontamination methods through an efficient and effective method that can be used continuously during normal operations of lighting fixtures and that does not interrupt activities over time. These embodiments allow for typical daily or terminal cleaning procedures to be supplemented with a consistent form of disinfection that can maintain facility cleanliness between these cleaning procedures and immediately combat new sources of contamination and the regular growth rates of microorganisms left behind after typical cleaning procedures.

In embodiments, it is possible to create a white light inclusive of the range of visible light (approximately 380-700 nm) that is advantageous because the complete spectrum can be used as a general illumination source to cause consistent bacterial inactivation when activated. According to embodiments of the disclosure, white light shall be defined as outlined above. The human ability to perceive light can vary greatly, but it is generally understood that the perceivable light spectrum comprises 380 nm to 700 nm, with the range varying by up to 30 nm depending on age, health, and other factors for each individual. Compared with ultraviolet (UV) light (another form of light-based microorganism inactivation), general illumination sources inclusive of the visible range of light have minimal effects on human health and in embodiments further described below, can be used in continuous exposure situations. UV is very effective in inactivating pathogenic bacteria, but medium-to-long-term exposure to the UV lights necessary for inactivating pathogenic bacteria can be detrimental to people, animals, plants, and even common materials used in every day products. For instance, many plastics and resins are susceptible to damage from continuous UV exposure.

An example device of the present disclosure is an overhead light source that emits white light inclusive of a visible light disinfection method that can replace typical overhead illumination sources in environments where environmental contamination must be controlled. The example device provides a similar illumination function to typical overhead illumination sources but also provides, through the modified light spectrum, disinfection that is suitable for continuous exposure at general illumination levels. This device of the present disclosure allows for the inclusion of a disinfection method directly into facilities that may have little effect or draw on operational requirements in a facility because illumination is already required in the environment.

Visible light disinfection mechanisms include activating endogenous molecules inside of microorganisms that can initiate inactivation through various methods. One of the existing methods is the use of light in the approximately 380-420 nm range to initiate a reaction with a porphyrin or porphyrin derivative to initiate cell death.

Using the approximately 380-420 nm peak wavelength light alone, which can include in some embodiments, a plus or minus 10 nm range, light disinfection embodiments can effectively inactivate microorganisms at levels that are considered safe for human exposure by many regulatory bodies. However, use of light within this range alone is not generally acceptable in application for continuous use of this light range as a source of general illumination.

Continuous exposure to the approximately 380-420 nm light alone would cause a strong violet discoloration inside of environments which would inhibit daily activities by negatively effecting general illumination characteristics. This method alone can be used effectively in unoccupied environments, but many environments with high occupancy rates would not be able to utilize maximum possible exposure times and dosages.

In embodiments of the disclosure, difficulties of creating a white light according to certain embodiments have been addressed. One difficulty includes that mixing two different ranges of light can produce white light if mixed and selected properly, but the characteristics of that light will not be acceptable for general illumination due to multiple factors of photometric and lighting concerns. For instance, mixing only two narrowband sources of light to make white typically leaves large gaps in what is considered the color rendering index. This factor causes only colors of objects and surfaces in the environment that match the two ranges of light to be illuminated properly, and other colored items to be viewed as abnormal. This fault leaves desire for higher quality light with a wider distribution of wavelengths that can reach a point of acceptability for general illumination.

Embodiments of the disclosure address white light capable of inactivating bacterial pathogens, wherein it has been discovered that the light can be effective by creating a white light with an acceptable color rendering index (CRI>50) may not be achieved, and having a high enough content of approximately 380-420 nm for significant antibacterial efficacy when used for general illumination.

Transition from Peak to xy Coordinates

Embodiments of the present disclosure have discovered that using peaks to denote mixing correlations is often less effective than using, as in regular color science, xy coordinates of the CIE 1931 (or other) chromaticity diagram. The use of peaks can result in failure in making white light. Switching from peaks to xy coordinates allows denoting a bounded area on, for example, the CIE 1931 xy color space diagram acceptable for mixing with 405 nm.

The present disclosure includes the identification of an xy coordinate range that can be used with mixing of approximately 380-420 nm to produce white lights in a color temperature range of 6000K to 2500K (very cool (stadium lighting) to very warm (incandescent lighting)) that are appropriate for acceptable general illumination, as illustrated in FIG. 1. The revised measurements detailed herein on aspects of choosing specific color coordinates for color mixing with visible light disinfection ranges is advantageous over the previous methods due to a higher level of reliability of the device to achieve acceptable white light when the methods are followed.

The color space on the CIE 1931 xy color space diagram is compacted in the approximately 380-420 nm range due to lower luminous sensitivity, allowing coordinate based mixing equations to function very effectively across the approximately 380-420 nm range and compensating for anticipated differences in diode or laser output in terms of exact peak, full width at half maximum (FWHM) of the source, and other irregularities that can be noticed in these emitters.

Using an xy chromaticity coordinate for a sample 400-405 nm diode as a basis for the calculation, the xy chromaticity coordinate is used as an approximation coordinate for any peak wavelength within the full color range of approximately 380-420 nm. The compaction of the color space in this region allows for the approximation to serve effectively with minimal error in application with the noted anticipated differences in output.

By the use of this approximation coordinate, the lines bounding the acceptable color coordinate area on the CIE 1931 xy color space diagram across the black body curve can be defined according to embodiments of the disclosure. This color coordinate area is used for emitting at one or more peak wavelengths, which are combined with the first light source(s) with a peak wavelength emission in the range of 380 nm to 420 nm. Both lines are plotted to intersect with the approximation coordinate in the approximately 380-420 nm range, and then each line respectively crosses the black body curve at 6000K and 2500K color temperatures, as illustrated in FIG. 1. The extensions of the lines from the black body curve, which is defined as a black body radiator, to the edge of color space yield two sides of the bounded area on the CIE 1931 xy color space diagram detailed in this device. The equations of the two bounding lines are approximately $y=2.23989x-0.382773$ and $y=1.1551x-0.195082$, wherein the y-intercept may include plus or minus 0.025 in some embodiments.

It is understood to yield a white light matched to the black body curve or another definition of white light approximate to the black body curve, that the color coordinate of the light mixed with the approximately 380-420 nm emitter must be on the opposite side of the black body curve from the approximately 380-420 nm approximation coordinate used to define the first two bounds and cannot pass the edge of color space on the side of the black body curve opposite the approximation coordinate. Thus, this arrangement defines the additional two bounds of the acceptable chromaticity coordinate range as the black body curve and the edge of the color space.

Color Rendering Index (CRI)

It has been demonstrated in embodiments of the current disclosure, that the generation of appropriate CRI spectra is possible. Thus, it has been discovered that it is possible to emit a white light acceptable for general illumination, defined as a CRI of greater than approximately 50, or even approximately 70, that kills bacteria. Embodiments of the present disclosure satisfy the requirements and emit white lights acceptable for general illumination with anti-bacterial properties.

While any amount of approximately 380-420 nm content in a light source may be capable of providing some disinfection on a surface, the luminous intensity required of the overall white light source that previous attempts emit would be required to be much higher than the devices of the present disclosure. The device and environments illuminated with the device would require significantly higher levels of overall illumination of white light to achieve the same effect as the devices of the present disclosure. For instance, previous lights as designed were incapable of providing effective white lighting and providing sufficient disinfection at general illumination levels at the same time due to the lack of content in the approximately 380-420 nm region.

According to some embodiments of the present disclosure, the approximately 380-420 nm range should comprise at least approximately 20% of the total combined output. In some embodiments, the approximately 380-420 nm range may comprise at least approximately 25%, 30%, 35%, 40%, 45%, or 50% of the total combined output. In a further embodiment, the approximately 380-420 nm range may comprise at least approximately 60% of the total combined output. It should be understood that this value will affect the quality of the white light, especially the CRI value. Accordingly, as the percent of the spectral output varies, the light source requires changes to the spectral output to maintain the white light desired.

According to some embodiments, a white light is generated that can inactivate microorganisms at proper intensities. In this disclosure, inactivation, in relation to microorganism death, shall be defined by a noted reduction in microorganism colonies or individual cells when exposed to light in question for a certain duration as compared to a control of the same organism in an identical setup and duration that is not exposed to significant amounts of light.

This white light composed by some embodiments is advantageous for use in environmental decontamination where people, plants, or animals are present since it does not alter the illumination characteristics of the environment as it was previously illuminated by general illumination sources such as incandescent, fluorescent, or LED lighting technologies for general illumination purposes.

Embodiments of the present disclosure include a light emitting device or fixture emitting sufficient intensity in the approximately 380-420 nm band of light to initiate cell death where when these wavelengths are combined with the possible addition of other wavelengths, the overall output of the light emitting device is perceived as white or a hue of white.

Embodiments of the present disclosure may utilize light emitting diodes and phosphor conversion technologies due to their relatively high electrical conversion efficacy, specific control of emission spectra as related to a phosphor, and wide market availability. Additional technologies, such as lasers and quantum dots, would also be acceptable for use in the present disclosure. It should be understood that phosphor conversion materials may comprise any now known or later developed phosphors or light converting chemistries capable of converting light from an emitter to the parameters disclosed herein, and a phosphor may include any known light conversion materials or molecules.

While a device using common LED lighting methods (RGB, phosphor conversion) can have a high lumens per watt for electrical efficiency, the heavy reliance on the blue diodes to sensitize the S cones of the eye is very effective in illumination due to luminous sensitivity characteristics of light and the human eye, but is largely not active in causing microorganism inactivation. Reliance on blue diodes to produce white light may not be advantageous to the disclosed methods due to the inherent design of blue diodes to be sensitive to the human eye, and not provide an alternative energy based function (microorganism inactivation). Yet blue is highly desired since it is a primary color used in eye sensitivity. Blue has been demonstrated in some example spectra to improve CRI up to acceptable CRI levels for general illumination when used synergistically in embodiments of the disclosure.

Embodiments of the disclosure can include arrangements/characteristics of light emitting devices as well as products using the spectra of light as described within this disclosure. Embodiments can also include spectrums of light that can fulfill what is described in the disclosure. It should be understood that these example spectra may be modified within reason for changes in light emitter selection/generation method, color temperature of the light, CRI or gamut area of the light, or the use of other light generation methods to accomplish similar characteristics as described for the spectrum.

Examples provided herein are based upon industry available light emitting diode technologies including both chip based semiconductor methods and phosphor conversion methods. Other existing light emitting technologies could also be used to generate similar spectrums fulfilling characteristics as described or new technologies may be used in the future.

In embodiments of the present disclosure, it should be understood that an "emitter" is an object emitting light, and includes semiconductor LEDs, phosphor converted LEDs, lasers, phosphor chemicals, quantum dots, gas emission technologies, etc. For example, phosphor and quantum dot materials as emitters when applied in an LED package or a remote phosphor package. Light emission methods include LED color mixing with one or more semiconductor sources. A modified example of color mixing is one combining both semiconductor and a conversion chemistry technology (phosphor, quantum dots). Laser emission sources can include any laser device emitting in the approximately 380-720 nm range. Light conversion chemistries include phosphors and quantum dots. Gas emission technologies include the use of mercury and neon. A device generating an acceptable light spectrum fitting to the disclosed embodiments could involve any possible mixture of these emitter technologies in a single device or multiple devices.

Embodiments can include emission methods comprising three-channel mixing, five-channel color mixing (red, green, blue, violet semiconductors paired with a blue pumped phosphor converted LED), a conversion-based LED package (a violet LED coated in a conversion chemistry (phosphor/QD) with a tuned emission causing white light inclusive of approximately 380-420 nm), laser-assisted white (an approximately 380-420 nm laser paired with LEDs mixed to make white), and two channel color mixing (a violet LED paired with an additional diode that when the two are mixed together, they produce white light). Many other combinations of technologies exist that are practicable under the stated claims and the combination of these embodiments can be understood by someone skilled in the art that they function similarly in factors of combining light to be guided by the following claims.

In embodiments, it should be understood that a "light fixture" or "light source" as used to define the final "device" includes the use of one or more materials, devices, configurations, groupings, and arrays to compose the "device." As used herein, "light fixture" typically refers to the entire device, while "light source" typically refers to the source of at least one peak wavelength, which in some embodiments may include any known device for creating light, such as an LED, a lamp, a laser, or any other known device for creating light. In some embodiments, the light source may further utilize an emitter or an emitter with an additional light conversion material, which can include a phosphor, a light converting chemistry, or the like. Lasers can be used in embodiments of the disclosure, including LED color mixing combinations (LEDs+light conversion chemistry, LEDs+lasers, and combination thereof). The "emitter" may refer to the underlying source of light within a light source, such as the LED or the laser, in some embodiments. Package architectures may include a converted LED package (e.g., a single LED/laser package using a combination of semiconductors and chemical conversion technologies) and remote conversion (remote placement of a chemical conversion technology in a luminaire design containing an LED or laser source). That is, the "light fixture" may have only a single emitter with multiple conversion technologies, or it may include multiple emitters, each with a single conversion technology or multiple conversion technologies.

Figure 2:
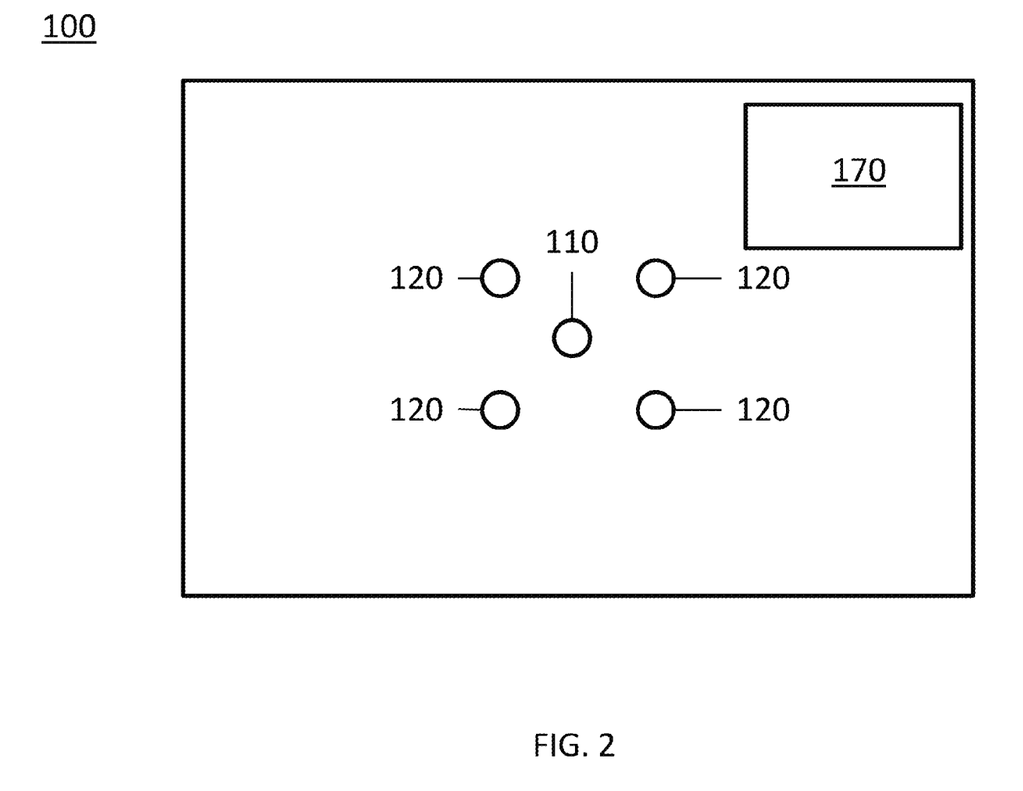
FIG. 2 illustrates a schematic diagram of a light fixture according to some embodiments of the disclosure.

As illustrated in FIG. 2, embodiments disclosed herein can include a light fixture 100. Light fixture 100 should be understood to include all light fixtures, lighting devices, or other nomenclature used throughout this disclosure. Light fixture 100 can comprise at least one first light source 110, or emitter, that emits at a peak in a range of approximately 380 nm to approximately 420 nm. Light fixture 100 can also include at least one second light source 120 that emits at a different wavelength. It should be understood that at least one second light source 120 may include one or multiple light sources, or may be combined with at least one first light source 110 in a single package. A combined light output of light fixture 100 can emit a colored light that is perceived as white light.

For instance, white light can be measured to include at least one of a CRI value of more than approximately 50, or in some embodiments more than 70, and a CCT value between approximately 1000K and approximately 8000K, or in some embodiments between approximately 2000K and approximately 6000K. At least one light source 120 can have an xy coordinate on the CIE 1931 xy color space within a bounded area defined by y=2.23989x−0.382773, y=1.1551x−0.195082 and above a black body curve (FIG. 1) which is mixed with the output of at least one first light source 110 to create a white light as defined by the CRI and CCT. These three measurements of light may be used alone or together in order to create and quantify a quality and color of white light of light fixture 100 according to embodiments of the disclosure.

Light fixture 100 may be used in a general lighting environment, examples of which will be detailed further below. Light fixture 100 may also be used in an agricultural lighting environment, a horticultural lighting environment, a therapeutic lighting environment, a medical lighting environment, a food processing lighting environment, or a hazardous lighting environment, including clean rooms and biological waste or processing environments. Light fixture 100 may be capable of completing the stimulation of all three tristimulus values of the human eye, as described previously. Light fixture 100 may have an overall output sufficient to inactivate at least one pathogenic microorganism. In some embodiments, light fixture 100 may include a combined light output that has an overall output containing a radiometric energy sufficient to inactive at least one bacterial population, or in some embodiments, a plurality of bacterial populations. For instance, the radiometric energy may include at least 0.01 mW/cm$^2$ at the surface of the lit area. It should be understood that the radiometric energy is related to the spectral energy content, described below.

In some embodiments, light fixture 100 has a combined light output including a proportion of spectral energy measured in the approximately 380 nm to approximately 420 nm range of greater than approximately 20%, and in some embodiments, greater than approximately 25%, 30%, 35%, 40%, 45%, or 50% of the total combined output. In a further embodiment, the approximately 380-420 nm range may comprise at least approximately 60%-70% of the total combined output. The spectral output is defined as the proportion of approximately 380-420 nm absolute irradiance value is divided over the 380-720 nm absolute irradiance value to yield a % spectral content of approximately 380-420 nm light. The spectral output is defined as the radiometric energy. The absolute irradiance values can be measured by any now known or later developed means. In some embodiments, the absolute irradiance values are measured in mW of radiometric energy.

Figure 3:
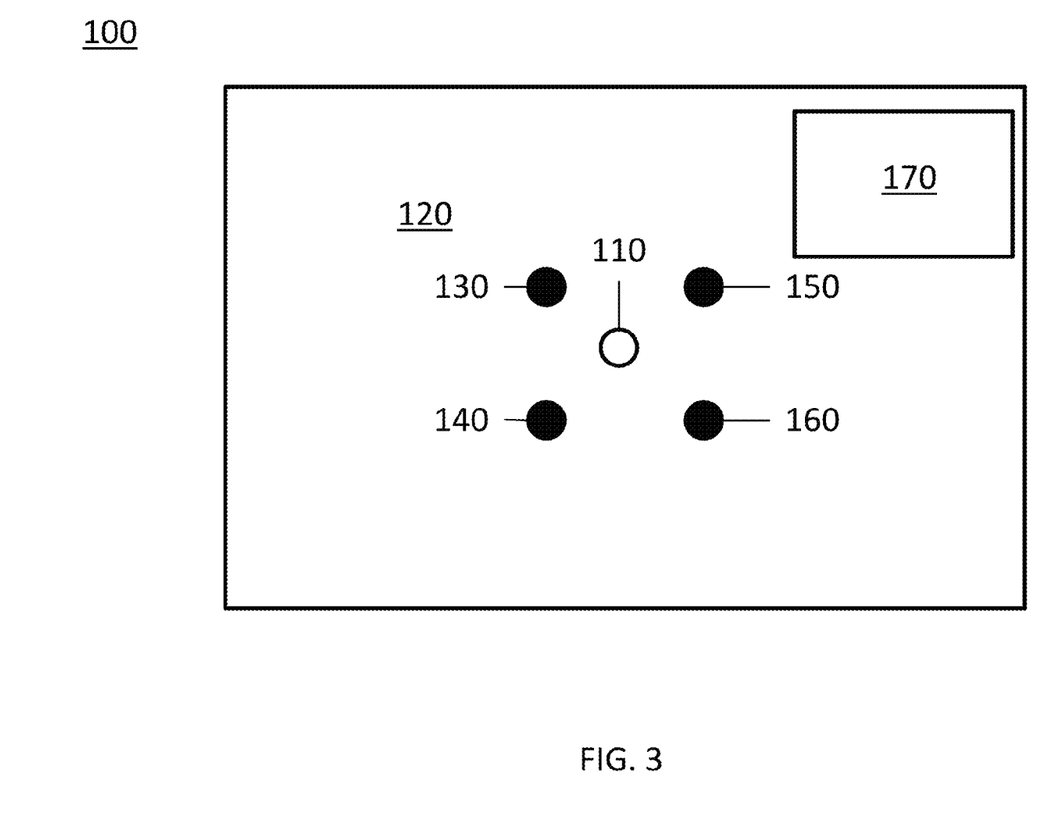
FIG. 3 illustrates a schematic diagram of a light fixture according to some embodiments of the disclosure.

In some embodiments, as illustrated in FIG. 3, the at least one second light source 120, shown as filled circles, that emits at a different wavelength can comprise a third light source 130 and a fourth light source 140. In further embodiments, third light source 130 and fourth light source 140 emit visible light. In further embodiments, at least one second light source 120 that emits at a different wavelength further comprises a fifth light source 150 and a sixth light source 160. In further embodiments, fifth light source 150 and sixth light source 160 emit visible light. As shown in FIG. 3, at least one second light source 120 includes third light source 130, fourth light source 140, fifth light source 150, and sixth light source 160. It should be understood, as disclosed previously, that any number of second light sources 120 can be used, and FIG. 3 is only illustrative.

In some embodiments, at least one first light source 110, at least one second light source 120, or some combination thereof, can include an LED. In some embodiments, at least one first light source 110, at least one second light source 120, or some combination thereof, can include a primary emitter and a secondary emitter. In such embodiments, the primary emitter can include an LED, a laser, a gas lamp, or some combination thereof, and the secondary emitter can include a semiconductor material, a phosphor, a Yttrium-Aluminum-Garnet (YAG) phosphor, a semiconductor nanocrystal, a quantum dot, or a combination thereof, or any other secondary emitter now known or later developed that can emit light pursuant to the disclosed embodiments of the present disclosure. The primary emitter may be an underlying light source, and the secondary emitter may be a color conversion technology, including any color conversion chemistries now known or later developed.

In some embodiments, light fixture 100 may further include a control system 170, control system 170 being capable of altering the combined light output. While shown within light fixture 100 in FIGS. 2 and 3, it should be understood that control system 170 may be within, external to, or in communication with light fixture 100. Control system 170 may include any control system, hardware, software, or a combination thereof, which allows for control of modulating the combined light output. For instance, control system 170 may increase or decrease the spectral content of approximately 380-420 nm light, and it may increase or decrease the emission of light emitted outside of the approximately 380-420 nm range. Control system 170 may also comprise a power supply. One example power supply 170 can include the LPF-60-12, made commercially by Mean Well.

In some embodiments, light fixture 100 can include further features and can be applicable to a number of applications as described below.

Reflector/Diffuser Components

Diffusers, reflectors, optics, protective shields, and other transmissive components of a light fixture or light bulb can contribute significantly to the overall efficiency of product function. While none of these materials has 100% transmission or reflection efficiency, the careful choice of material(s) may be of value in lighting design to obtain high efficiencies for an effective and efficient product. Many plastics, glasses, coatings, and other materials are acceptable for reflectors or transmissive components for general illumination sources, such as incandescent bulbs, fluorescent bulbs, and RGB/blue-phosphor LEDS. These lighting sources rely very little on near-UV wavelengths in product function.

However, many of these reflectors or transmissive components exhibit a sharp drop off in reflectance or transmission efficiency (sometimes close to zero) for wavelengths of light in the near-UV range, e.g., the λ=approximately 380 to approximately 420 nm of embodiments of the disclosure. Thus, light sources in which light in the λ=approximately 380 to approximately 420 nm range is a component of the illumination that can show significant losses with the incorrect use of reflective or transmissive materials in light bulb or light fixture design. Reflector and transmissive materials must be selected appropriately based on the output of light from the light source in question.

In embodiments where a light containing a significant proportion of λ=approximately 380 to approximately 420 nm light, suitable reflective surfaces or reflector optics have less than approximately 30% loss of energy after a single reflectance of light in the λ=approximately 380 to approximately 420 nm range, and a solid transmissive material should have less than approximately 30% loss of energy after transmission of light in the λ=approximately 380 to approximately 420 nm range. Furthermore, the portion of light in the λ=approximately 380 to approximately 420 nm range should be sufficient to illuminate an object outside of the fixture with at least approximately 0.005 mW/cm² of light in the λ=approximately 380 to approximately 420 nm range. These characteristics are relevant, for example, where the light source is an LED or combination of LEDs, the light source is an LED or a combination of LEDs and other light sources or emitters (e.g., phosphors, lasers), the light source is a laser diode, the reflective material is positioned directly or indirectly in the path of light from the source, the reflective material may be used for the mixing of light, the reflective material may be used to control the distribution of light, or the transmissive material is used as a lens, a diffuser, an optical component, as a cover or protective shield, and/or to control the distribution of light. In these embodiments, any reflector or diffuser should include a material that will allow the most approximately 380-420 nm light to emit, and can include any material capable of not substantially absorbing light in the 380 nm to 420 nm range. In some embodiments, this may include plastics, resins, thermoplastic resins, or polymers which do not substantially absorb light in a range of 380 nm to 420 nm.

In embodiments of the present disclosure, lighting fixture 100 emits light within the visible spectrum (k=approximately 380 to approximately 700 nm) and contains sufficient radiometric energy for the inactivation of one or more bacteria, and the light emitted from the light fixture is appropriate for general illumination purposes; the correlated color temperature (CCT) of the light emitted from the fixture is from about 1000 K to about 8000 K, and the color rendering index (CRI) is at least about 50. These characteristics according to embodiments of the disclosure can be utilized in many lighting applications. The following examples are not meant to be limiting. It should be understood that nearly any lighting application could be applicable with minor alterations to light fixture 100 in order to fit the criteria of said applications.

For example, embodiments of the disclosure may be applicable in a number of applications. These applications can include situations wherein: the light fixture is designed appropriately to fit into a drop ceiling framing structure with square or rectangular grid openings, the light fixture is recessed into the drop ceiling framing structure with proper installation, the product fits into a US standard 2'×2' drop ceiling opening, the product fits into a US standard 2'×4' drop ceiling opening, the light fixture has an adapter to fit into alternatively sized drop ceiling openings or other international standards of light fixtures, the light fixture may be designed appropriately to mount into a circular cutout of a panel held in a drop ceiling framing structure, or to mount into a circular cutout of an alternative ceiling structure, such as drywall or other solid ceiling structures, the light fixture may be hanging from the ceiling, or suspended below the ceiling by a secondary suspension method or structure.

In some embodiments, light fixture 100 may be applicable in a number of applications including, wherein: the light fixture may be directly mounted on the ceiling, the light exiting the fixture may be distributed in a "spot" distribution, the light exiting the fixture may be distributed in a "batwing" distribution, the light fixture contains one or multiple light emitting element(s), the light fixture contains one or more groups of light emitting element(s), the light-emitting elements or groups of light-emitting elements may be individually replaceable, the light fixture contains access to components from a room-facing access point, the light fixture contains a physical digital access point (e.g., USB, firewire, serial, Ethernet, phone) compatible with components in the light fixture, and the light fixture contains a wireless access method compatible with components in the light fixture.

In embodiments of the disclosure, light fixture 100 can be useful in a plethora of applications. Some of the applications are listed below, but it is understood that these are examples of applications. The list is not intended to be exhaustive.

Livestock Rearing and Agriculture

In the cultivation of livestock and agricultural products, contamination from bacteria, fungi, or viruses can cause losses of animal life, plant life, and/or spoilage of rendered products. Common production practices now pack animals and plants densely for efficiency, in terms of space and finances, yet contamination from microorganisms can spread rapidly in such an environment, with infection spreading between plants or animals.

Currently, there is extensive use of pesticides, antibiotics, and chemical cleaners to prevent loss of final product by preventing contamination of animals or agriculture products, yet animal and plant losses, final product losses, and the unknown distribution of contaminated final products is still an issue faced by the industry. Thus, there is a continuing need for better methods to control microorganisms in the cultivation environment and processing facilities to prevent loss of final product.

Environmental cleaning of these areas or the animals and plants is sometimes conducted intermittently to mitigate the growth and spread of these contaminants, but is never fully effective. Thus, there is a continuing need for methods to control microorganisms in the cultivation environment and processing facilities to prevent loss of final product.

In an embodiment of the present disclosure, a lighting unit using λ=approximately 380 to approximately 420 nm light mixed with at least one second wavelength to produce white light is effective in inactivating bacterial, fungal, and/or viral species to prevent the contamination of the cultivation environment and/or infection of the animal or agriculture product.

It is widely known that UV light can consistently inactivate microorganisms in a cultivation environment. However, UV is detrimental to animals and plants too. Light of λ=approximately 380-420 nm light is safe for both animals and plants, and devices of the present disclosure allow for safe and consistent protection of the cultivation environment from microorganisms that has not before been possible previously. By illuminating animals, plants, and the environments they are housed, stored, and processed in, microorganisms can be reduced or eliminated, reducing or eliminating spoilage, sickness, and/or infection. The device may also illuminate fluid or food supply points and methods of transportation to help prevent cross contamination of animals and plants. In greenhouse production, for example, the device may illuminate plants, their nutrient feeding systems, and the entire enclosed environment they are cultivated in to protect the plants from spoilage, infection, and/or diseases. The device may also illuminate processing and harvesting facilities and equipment.

In an embodiment of the present disclosure, a lighting fixture emits light within the visible spectrum (λ= approximately 380 to approximately 700 nm) and contains sufficient radiometric energy for the inactivation of one or more bacteria, and the light emitted from the light fixture is appropriate for general illumination purposes; the correlated color temperature (CCT) of the light emitted from the fixture is from approximately 1000 K to approximately 8000 K, and the color rendering index (CRI) is at least approximately 50.

Specifically, a λ=approximately 380 to approximately 420 nm light, mixed with at least one second wavelength to produce white light, sufficient to inactivate bacterial, fungal, and/or viral organisms, or a white light with a component of λ=approximately 380 to approximately 420 nm, mixed with at least one second wavelength to produce white light, sufficient to inactivate bacterial, fungal, and/or viral organisms, is directed in an environment containing commercial animals/flora that are susceptible to bacterial-, fungal-, and/or viral organism-related illnesses and conditions or environmental contamination (e.g., mold growing in pens, algae growing in fish tanks, hydroponic/aeroponic/aquaponic plant growth environment contamination). These characteristics can be applied according to some embodiments, for example, where the flora/animals are enclosed or protected by a structure, the light is distributed onto animals, plants, and/or surfaces in the environment, the light illuminates air or fluids circulating through the animal/flora environment, the light illuminates the roots, leaves, flowers, stems, and/or fruits of a plant being cultivated, and the light illuminates surfaces used in the transport, movement, or production tasks required for animal/plant cultivation (e.g., animals: killing floor, cutting stations, transport ramps, treatment areas, packaging. Plants: harvest area, trimming, collection, packaging).

Food Displays

In the retail sale of food, fresh products are commonly displayed to customers in the shopping environment. In many retail stores, the products are stored on shelves and in cases with viewing windows. Many of these products are considered perishable, with a very short shelf life like meat, produce, or fish. The short shelf life of these items is due to the degradation of the quality of the product over the time displayed. This degradation of the product is caused by a variety of factors: breakdown of cells or molecules due to aging, loss of water or other volatile components into the air, or spoilage based on bacterial, fungal, or viral contamination.

Embodiments of the present disclosure include a device to reduce bacterial, fungal, and/or viral contamination on the surfaces of fresh products and in the environment they are stored in. With a lighting unit producing light in the λ=approximately 380 to approximately 420 nm range, mixed with at least one second wavelength to produce white light, common bacteria can be inactivated. With an illumination source emitting this light or a light with a component in that range sufficient to inactivate bacteria, fungi, and/or viruses, these organisms can be reduced or eliminated on the surfaces of fresh products and their packaging. The elimination of these organisms on the surfaces or the environment of the display cases and the product themselves also aids in reducing the spread of pathogenic organisms that are linked to serious food-borne illnesses, such as *E. coli* or *Salmonella* spp.

Embodiments of the present disclosure include a lighting unit that emits λ=approximately 380 to approximately 420 nm light, mixed with at least one second wavelength to produce white light, sufficient to inactivate bacteria, fungi, or viruses, or a white light with a component in the range of λ=approximately 380 to approximately 420 nm sufficient to inactivate bacteria, fungi, or viruses directed to an environment containing foods displayed for sale that are susceptible to bacterial, fungal, or viral contamination. These characteristics can be applied according to some embodiments, for example, where the product is positioned to illuminate the surfaces of the food in the display unit, the product is positioned to illuminate the surfaces of the display unit, the product is positioned to illuminate the surfaces of food packaging in the display unit, the food is displayed in a shelving style unit, the food is displayed in a shelving style unit that is open to the surrounding shopping environment, the food is displayed in a shelving style unit that is temperature controlled, the food is displayed in a shelving style unit that is humidity controlled, the light source is integrated into the food display unit as supplementary or primary illumination, the food is displayed in an enclosure with a transparent viewing portion, the enclosure is temperature controlled, the enclosure is humidity controlled, the product emitting light is inside of an enclosure, and the product emitting light is outside of an enclosure emitting light into the enclosure.

Storage

Controlled environments are required for many purposes, such as the preservation of food products, the aging of goods, such as wines, liquors, and tobacco products, or the general prevention of contamination during many industrial processes. Such environments are protected and controlled in many different manners, including in terms of air quality, temperature, humidity, and particle count.

Perishable food is commonly stored in refrigerated enclosures to slow degradation of the food and to slow bacterial growth that can cause food spoilage and food sickness. While refrigeration alone can extend food life and quality, compared with room temperature storage, bacteria and molds can still be common destroyers of food in these environments, in a home refrigerator just as in an industrial meat locker.

Humidors are humidity controlled environments, commonly associated with the storage or aging of cigars and tobacco products, that maintain moisture content at a set level for the items stored in the enclosure. However, bacterial and mold spoilage of these goods can occur in the event of contamination, resulting in the loss of what is typically a high value product.

In clean rooms, efforts are made to control the amount of particles in the air in a given enclosure. Most function by continuously pumping in filtered air and forcing the exodus of airborne particles. Bacterial growth and the generation of bacteria or mold spores from contaminated sites can continuously generate particles in the environment that can be difficult to prevent and cause costly contamination issues in high-value products undergoing processing or storage in the environment.

All of these controlled environments and their contents can be negatively affected by the presence of bacteria, fungi, and/or viruses, and thus it is desirable to prevent their growth and presence with an effective method. Embodiments of the present disclosure include lights in the λ=approximately 380 to approximately 420 nm range that have been shown to be effective in inactivating bacteria, fungi, and/or viruses, yet are safe for the presence of people. This arrangement allows use of the device to create an environment that is better protected than a standard controlled environment, and also still allows for human interaction and entrance into the environment.

Embodiments of the present disclosure include light sources that emit λ=approximately 380 to approximately 420 nm light, mixed with at least one second wavelength to produce white light, of sufficient intensity to inactivate bacteria, fungi, and/or viruses, or white light with a component in the range of λ=approximately 380 to approximately 420 nm sufficient to inactivate bacteria, fungi, and/or viruses directed to an environment containing products stored in an enclosure with a controlled environment that are susceptible to bacterial, fungal, and/or viral contamination. These characteristics can be applied according to some embodiments, for example, where the light source is positioned to illuminate the surfaces of the susceptible products in the enclosure, the light source is positioned to illuminate the surfaces of the packages of susceptible products in the enclosure, the light source is positioned to illuminate the surfaces of the enclosure, the enclosure is a refrigerated environment, the enclosure is a humidity controlled environment, the enclosure is a heated environment, the enclosure is a particle count controlled environment, the enclosure is an air quality controlled environment, the light source is integrated into the enclosure as supplementary or primary illumination, the light source is positioned to illuminate into an internal storage or organization area.(refrigerator bins), the light source is incorporated into the structure of the enclosure, a control system is incorporated to activate or deactivate the light source, a control system is incorporated to activate or deactivate the light source based on the position of a certain portion of the structure of the enclosure (i.e., door/switch), and a control system is incorporated to activate or deactivate the light source based on the input of a person.

Food Production

In a food preparation environment (e.g., restaurants, industrial kitchens, fast food, prepared goods store, for direct sale or delivery to the consumer/customer) bacteria, fungi, and/or viruses pose issues of spoilage, pathogenic contamination, and infection, and can be a serious issue for the establishment. These contamination issues can come from a large variety of sources in such an open environment: e.g., personnel, customers, raw materials, air systems, and water. While many cleaning practices have typically been implemented at these sites, contamination and infection outbreaks are still seen. Typically, these contamination issues are only noticed after the damage is done, when inventory is spoiled or customers are sick.

Embodiments of the present disclosure include devices that can help consistently to reduce bacterial, fungal, and/or viral organisms in multiple sensitive areas in the foodservice environment, using light in the range of $\lambda$=approximately 380 to approximately 420 nm mixed with at least one second wavelength to produce white light. Embodiments of the present disclosure include a lighting device that exposes a kitchen work station or surface used in the production and preparation of food or food service goods exposed to a light that has a portion of its emissions in the $\lambda$=approximately 380 to approximately 420 nm range, mixed with at least one second wavelength to produce white light, sufficient to inactivate pathogenic bacterial, fungi, and/or viruses related to spoilage or degradation of food products. These characteristics can be applied according to some embodiments, for example, where the light source is positioned to illuminate surfaces and items in a refrigerated environment, the light source is positioned to illuminate surfaces that come in contact with food products or food packages, the light source is positioned to illuminate surfaces at work stations, tables, or counters, the light source is positioned to illuminate transaction terminals with customers, the light source is positioned to illuminate equipment controls, the light source is positioned to illuminate equipment used in the preparation of food, the light source is positioned to illuminate storage containing food products or storage containing equipment required to prepare food products, the light source is positioned to illuminate a surface that food being prepared contacts, the light source is positioned to illuminate a surface that a food package or container contacts, the light source is positioned to illuminate dispensing containers and dispensing equipment of food products, the light source is positioned to illuminate utensils (forks, cups, plates, napkins) or condiments at a site available to the customer, the light source is positioned to illuminate drink dispensing equipment and surfaces, the light source is installed above head height to illuminate one or more noted surfaces, and the light source is installed to illuminate surfaces on a grill, burner arrangement, oven rack, or other cooking surface that comes in direct contact with food.

Control System

With the growth of LED technology in lighting, many more options for modulation are now available for controlling a light source for a variety of desired purposes. While any standard light source may have its intensity controlled or be placed on a timer or switch, the use of new LED lighting, and specifically color mixing technologies used in generation of white light, allow for a much wider range of control of the light generated and the overall operation of a light source. New advances that make web and computer access nearly consistently available (e.g., mobile phones, tablets) also allow for direct modulation of these characteristics of lights by a user from a connected device, providing the capability is established.

Increased knowledge of phototherapy, disinfection, circadian rhythms, sleep, memory and other health-related issues have all been linked to factors including light in the visible spectrum. To this end, it is desirable to control these variables to allow a user to gain desired effects of lighting or to be exposed to lighting on a plan established to improve well-being.

By using a multi-colored source, different regions of the visible spectrum can be modified to provide more or less radiation from specific regions of light to cause wellness benefits through light absorption by the human body or the reduction of bacterial pathogens through visible light disinfection. For example, a control system can modulate and alter light emitted from a light source for a patient, elderly, or child care environment, to provide the benefit of increased well-being. These characteristics can be applied according to some embodiments, for example, where control system 170 can control one or multiple light sources, either individually or as a group. Control system 170 can modulate the CCT between approximately 1000 K to approximately 8000 K for the light emitted from light fixture 100. Control system 170 can modulate the intensity of the light fixture 100. Further, control system 170 can modulate the intensity of one or multiple ranges of wavelengths seen to have therapeutic health benefits or control system 170 can modulate the CCT of the light based on therapeutic recommendations. Control system 170 can change the color of the light emitted and can modulate or alter light based on a timer. Control system 170 can be controlled by a patient or guest, including being controlled by a patient or guest through a mobile phone, tablet, or other networked device. Control system 170 can also be controlled by an employee, including being controlled by an employee through a mobile phone, tablet, or other networked device, and the employee may have the ability to override the control inputted by the patient. A stand-alone unit can modulate control system 170 from inside the room, a stand-alone unit can modulate one or multiple control systems in a facility from a central or virtual location. Control system 170 may alter pulse width modulation parameters of one or multiple elements used in light fixture 100 to achieve the desired modulation of light emitted from light fixture 100. Control system 170 may alter constant current parameters of one or multiple elements used in light fixture 100 to achieve the desired modulation of light emitted from light fixture 100, and control system 170 may be able to receive active feedback from measurement systems.

Industrial Processes

UV light can be used for disinfection in an industrial environment, but not in environments where personnel would also be exposed to the light, for safety reasons. This greatly limits the ability to create a consistently protected environment against bacteria. UV light also has known detrimental effects on plastics, proteins, and DNA, potentially degrading goods, raw materials, packaging, and equipment in the industrial environment.

Loss of goods and raw materials occurs in many industrial processes because of bacterial, viral, or fungal infections or contamination, including, but not limited to, pharmaceuticals, brewing/distillation, food production, food packaging, chemical processing, and semiconductor processing steps requiring a clean room environment.

Embodiments of the present disclosure include a device to prevent bacterial, viral, or fungal infections or contamination by inactivating these organisms with light in the $\lambda$=approximately 380 to approximately 420 nm range mixed with at least one second wavelength to produce white light. The device of the present disclosure may be used on raw materials, in the production process, during the packaging process, or on any equipment used. The device may also be used to create a more sanitary environment around sensitive equipment or goods.

Embodiments of the present disclosure include a lighting unit that emits light over a manufacturing, assembly, processing, production, or packaging process or related goods in the $\lambda$=approximately 380 to approximately 420 nm range, mixed with at least one second wavelength to produce white light, sufficient to inactivate bacteria, fungi, and/or viruses. These characteristics can be applied according to some embodiments, for example, where the light source is used to continually inactivate bacteria, fungi, and/or or viruses in a production environment, the light source is used to inactivate bacteria, fungi, and/or viruses on the surfaces of a package or inside of a package, the light source is used to inactivate bacteria, fungi, and/or viruses on equipment surfaces used to handle packages or material used to create packages, the light source is used to inactivate bacteria, fungi, and/or viruses on equipment surfaces used to transport or place goods into packages, the light source is used to inactivate bacteria, fungi, and/or viruses on equipment surfaces used to create goods or modify raw materials, the light source is used to inactivate bacteria, fungi, and/or viruses on equipment surfaces used to store goods, raw materials, or intermediate forms of goods, and the light source is used to inactivate bacteria, fungi, and/or viruses on or in goods, raw materials, or intermediate forms of goods.

LED Bacterial Pathogen Inactivation

Inactivation of microorganisms using methods involving exposure to light is an area of increasing research interest. Common methods of bacterial inactivation include using disinfection, e.g. bleach, and ultraviolet (UV) light. UV light is well established as a light inactivation treatment; however, UV light has major drawbacks such as DNA damage, primarily as a result of UV absorption by DNA. In addition, quality control (QC) and calibration of the use of UV as a method of inactivation is time-consuming and labor-intensive. Embodiments of the disclosure demonstrate that bacterial organisms are susceptible to an array of light-emitting diodes (LED) emitting light of a wavelength of approximately 380-420 nm.

In order to demonstrate this, three bacterial organisms were evaluated for inactivation under various conditions. A 1.0 McFarland suspension was made of *Streptococcus pyogenes*, *Escherichia coli* O157:H7, and methicillin-resistant *Staphylococcus aureus* (MRSA). Neat sample suspensions contained approximately 108 CFU/mL of bacteria. Seven 10-fold dilutions were prepared and subsequently placed onto a mass spectrometer (MS) sample plate. The first set of samples, were placed under the 10 mW/cm2 LED array for 4 hours. After 4 hours, the kill rates for *E. coli* and MRSA ranged from 91-100%.

To increase the kill rate efficiency, the bacterial organisms were tested utilizing a tissue culture plate (TCP). Tissue culture plates have wider and shallower wells in comparison to the MS plates. A micro-magnetic stir bar was added to each well ensuring that light could penetrate all layers of the bacterial suspension equally. After a four hour incubation at 10 mW/cm2, the kill rates for *E. coli* and MRSA increased to approximately 99-100% (Table 1).

TABLE 1

Killing efficiency at 10 mW/cm$^2$ for 4 hours with TCP

| Initial Concentration (CFU/100 µL) | E. coli | MRSA | S. pyogeness |
|---|---|---|---|
| $10^1$ | 100 | 100 | N/A |
| $10^2$ | 100 | 100 | 100 |
| $10^3$ | 99.93711 | 100 | 100 |
| $10^4$ | 99.98742 | 100 | 100 |
| $10^5$ | 99.98868 | 100 | 100 |
| $10^6$ | 99.98289 | 100 | 100 |
| $10^7$ | 99.98289 | 99.99954 | 100 |

With successful inactivation after 4 hours, the time of inactivation was reduced to 62.5% to 1.5 hours. Both *E. coli* and MRSA were tested for 1.5 hours at 10 mW/cm2. Efficiencies were comparable to the four hour trials (Table 2).

TABLE 2

Killing efficiency at 10 mW/cm2 for 1.5 hours

| Initial Concentration (CFU/100 µL) | S. pyogenes | MRSA |
|---|---|---|
| $10^1$ | N/A | 100 |
| $10^2$ | 100 | 100 |
| $10^3$ | 100 | 99.9187 |
| $10^4$ | 100 | 99.87805 |
| $10^5$ | 100 | 99.87805 |
| $10^6$ | 100 | 99.87805 |
| $10^7$ | 99.90583333 | 99.87805 |

The last set of experiments aimed at reducing the power of the LED while still maintaining high bacterial killing efficiencies. The power of the LED array was reduced from 10 mW/cm2 to 0.50 mW/cm2 and finally to 0.25 mW/cm2.

For both sets of experiments, the time of incubation was increased to 16 hours. Even though the power was reduced both 20× and 40× the initial power, 99% of the bacterial was killed (Table 3).

TABLE 3

Killing efficiency at varying powers for 16 hours

| Initial Concentration (CFU/100 μL) | 0.50 mW/cm² MRSA | 0.25 mW/cm² | E. coli |
|---|---|---|---|
| $10^1$ | 100 | N/A | N/A |
| $10^2$ | 97.84946 | 99.47917 | 98.9418 |
| $10^3$ | 99.89247 | 99.89583 | 100 |
| $10^4$ | 99.68817 | 99.48438 | 99.47619 |
| $10^5$ | 99.64839 | 99.87865 | 99.47143 |
| $10^6$ | 99.64839 | N/A | N/A |
| $10^7$ | 99.64839 | N/A | N/A |

Further studies carried out have demonstrated that at 500 lux to 1000 lux of white light according to embodiments of the disclosure, a 99.7% reduction of the amount of bacteria (*Staph. aureus*) on either plastic or steel can be achieved. At 500 lux, a 99.7% reduction was achieved after 14 hours. Further, after only two hours, the bacteria count was already approximately 94% lower than in control groups.

Additional studies were carried out utilizing a light fixture according to embodiments of the disclosure installed in a public restroom in a high traffic area. Microbial readings were conducted using a 3M Luminometer at approximately 5 PM (before cleaning) and approximately 8 AM (after cleaning) and recorded in Relative Light Unit (RLU) units, measuring adenosine triphosphate (ATP) on a swab, which is an indicator of bacterial presence. Data was collected from three points inside the room, the sink, toilet seat, and inside door handle, and from one point outside of the room, the outside door handle, in order to show standardized cleaning methods. It should be understood that ATP and bacteria levels are not necessarily directly proportional to one another, but that a large drop in ATP is typically indicative of a significant drop in bacteria count.

The data collected showed that the room was 92.4% cleaner using an average percent change during the course of the study. Over the course of the day, the RLU count would grow on average by 22.1% as compared to 1156% prior to installation of the lighting fixture according to embodiments of the disclosure. Further, before installation, RLU rates consistently failed at the door and the toilet seat, as well as the average of all 3 measure sites, where the suggested standard that anything over 1000 RLU fails in cleanliness and it is recommended that the passing cleanliness level is based on a goal of 250 RLU. Following installation, all three were below the 1000 RLU count, and not a single failing event was recorded. Further, all sites showed less than the 250 RLU cleanliness goal as well.

As such, it has been demonstrated that utilizing embodiments of the present disclosure, a solid state light fixture can decrease human exposure to pathogenic bacteria whilst emitting what can be perceived by the human eye as a white light in a range of color temperatures.

The foregoing description of various aspects of the disclosure has been presented for the purpose of illustration and description. It is not intended to be exhaustive or to limit the disclosure to the precise form disclosed, and obviously, many modifications and variations are possible. Such variations and modifications that may be apparent to one skilled in the art are intended to be included within the scope of the present disclosure as defined by the accompanying claims.

What is claimed:

1. A light fixture comprising:
   at least one first light source that emits at a peak wavelength in a range of approximately 380 nanometers (nm) to approximately 420 nm;
   at least one second light source that emits at a different peak wavelength, wherein a combined light output of the at least one first light source and the at least one second light source emits a colored light that is perceived as white light;
   wherein the white light comprises a color rendering index (CRI) value of more than approximately 50;
   wherein the at least one second light source that emits at a different peak wavelength consists of: an xy coordinate on a International Commission on Illumination (CIE) 1931 xy color space diagram above a black body curve within a bounded area defined by a first line of approximately $y=2.23989x-0.382773$ and a second line of approximately $y=1.1551x-0.195082$; and
   wherein the combined light output has a proportion of spectral energy measured in the approximately 380 nm to approximately 420 nm range of greater than approximately 20%.

2. The light fixture of claim 1, wherein the at least one first light source emits at a peak wavelength in the range of approximately 400 nm to approximately 410 nm.

3. The light fixture of claim 1, wherein the white light comprises a CRI value of more than approximately 60.

4. The light fixture of claim 1, wherein the white light comprises a CRI value of more than approximately 70.

5. The light fixture of claim 1, wherein the white light comprises a CRI value of more than approximately 80.

6. The light fixture of claim 1, wherein the white light comprises a CRI value of more than approximately 90.

7. The light fixture of claim 1, wherein the white light comprises a CRI value of approximately 100.

8. The light fixture of claim 1, wherein the white light further comprises a correlated color temperature (CCT) value between approximately 1000K and approximately 8000K.

9. The light fixture of claim 5, wherein the white light comprises a CCT value between approximately 2000K and approximately 6000K.

10. The light fixture of claim 1, wherein the at least one second light source that emits at a different peak wavelength consists of: an xy coordinate on a International Commission on Illumination (CIE) 1931 xy color space diagram within a bounded area defined by a first line of approximately $y=2.23989x-0.382773$, a second line of approximately $y=1.1551x-0.195082$, and above a third line of $y=-2.57862x^2+2.58744x-0.209201$.

11. The light fixture of claim 1, wherein the at least one first light source that emits at a peak of approximately 380 nm to approximately 420 nm has an overall output sufficient to inactivate at least one pathogenic microorganism.

12. The light fixture of claim 1, wherein the combined light output has an overall output containing a radiometric energy sufficient to inactive at least one bacterial population.

13. The light fixture of claim 1, wherein the combined light output has a proportion of spectral energy measured in the approximately 380 nm to approximately 420 nm range of greater than approximately 25%.

14. The light fixture of claim 1, wherein the combined light output has a proportion of spectral energy measured in the approximately 380 nm to approximately 420 nm range of greater than approximately 30%.

15. The light fixture of claim 1, wherein the combined light output has a proportion of spectral energy measured in the approximately 380 nm to approximately 420 nm range of greater than approximately 35%.

16. The light fixture of claim 1, wherein the combined light output has a proportion of spectral energy measured in the approximately 380 nm to approximately 420 nm range of at least approximately 40%.

17. The light fixture of claim 1, wherein the at least one second light source that emits at a different wavelength comprises a third light source and a fourth light source.

18. The light fixture of claim 13, wherein the third light source and the fourth light source emit visible light.

19. The light fixture of claim 13, wherein the at least one second light source that emits at a different wavelength further comprises a fifth light source and a sixth light source.

20. The light fixture of claim 15, wherein the fifth light source and the sixth light source emit visible light.

21. The light fixture of claim 1, wherein the at least one first light source comprises a light emitting diode (LED).

22. The light fixture of claim 17, wherein the at least one first light source comprises a primary emitter and a secondary emitter.

23. The light fixture of claim 18, wherein the primary emitter comprises a light emitting diode (LED) and the secondary emitter comprises at least one of a group consisting of: a semiconductor material, a phosphor, a Yttrium-Aluminum-Garnet (YAG) phosphor, a semiconductor nanocrystal, and a quantum dot.

24. The light fixture of claim 1, further comprising:
   a control system, the control system configured to alter the combined light output.

\* \* \* \* \*